(12) United States Patent
Kitakaze

(10) Patent No.: US 7,026,293 B2
(45) Date of Patent: Apr. 11, 2006

(54) TREATMENT OR PROPHYLAXIS OF ISCHEMIC HEART DISEASE

(75) Inventor: Masafumi Kitakaze, Izumi (JP)

(73) Assignee: Daiichi Suntory Pharma Co., Ltd., Tokyo (JP)

( * ) Notice: Subject to any disclaimer, the term of this patent is extended or adjusted under 35 U.S.C. 154(b) by 228 days.

(21) Appl. No.: 09/752,724

(22) Filed: Jan. 3, 2001

(65) Prior Publication Data

US 2001/0027181 A1 Oct. 4, 2001

(30) Foreign Application Priority Data

Mar. 31, 2000 (JP) .................................. 2000-098134

(51) Int. Cl.
*A61K 38/00* (2006.01)
*A61K 38/24* (2006.01)
*C07K 14/00* (2006.01)

(52) U.S. Cl. ............................ 514/12; 514/13; 530/300; 530/399

(58) Field of Classification Search ................ 530/300, 530/399; 514/12, 13
See application file for complete search history.

(56) References Cited

PUBLICATIONS

Feit et al. "Inherency in patent law," J. Pat. Trade. Off. Soc., vol. 85, No. 1, pp. 5–21, 2003.*
Takata et al., "The beneficial effects of atrial natriuretic peptide on arrhythmias and myocardial high–energy phosphates after reperfusion", Cardiovascular Research, 32, 286–293, 1996.*
Arimura et al., *Biochemical and Biophysical Research Communications*, vol. 174, No. 1, pp. 142–148 (1991).
Furuya et al., *Biochemical and Biophysical Research Communications*, vol. 170, No. 1, pp. 201–208 (1990).
Furuya et al., *Biochemical and Biophysical Research Communications*, vol. 177, No. 3, pp. 927–931 (1991).
Kangawa et al., *Biochemical and Biophysical Research Communications*, vol. 118, No. 1, pp. 131–139 (1984).
Kangawa et al., *Biochemical and Biophysical Research Communications*, vol. 121, No. 2, pp. 585–591 (1984).
Minamitake et al., *Biochemical and Biophysical Research Communications*, vol. 172, No. 3, pp. 971–978 (1990).
Sudoh et al., *Biochemical and Biophysical Research Communications*, vol. 159, No. 3, pp. 1427–1434 (1989).
Sudoh et al., *Biochemical and Biophysical Research Communications*, vol. 168, No. 2, pp. 863–870 (1990).
Yoshihara et al., *Biochemical and Biophysical Research Communications*, vol. 173, No. 2, pp. 591–598 (1990).
Hidaka et al., *Folia Pharmacol. Japan*, 101 pp. 309–325 (1993), and a partial translation of the relevant position.

* cited by examiner

*Primary Examiner*—Jon Weber
*Assistant Examiner*—Rita Mitra
(74) *Attorney, Agent, or Firm*—Hunton & Williams LLP

(57) ABSTRACT

The present invention provides a pharmaceutical composition and a method for reducing an infarct region resulting from the ischemic necrosis of cells, especially, a pharmaceutical composition and a method for suppressing ischemia-reperfusion injury in the treatment of ischemic heart disease. The pharmaceutical composition and the method utilize a substance, as an active ingredient, which can increase intracellular cGMP production by acting on a natriuretic peptide receptor, and which has the effect of reducing an infarct region. The substance is preferably a natriuretic peptide. The present invention is particularly useful for the treatment or prophylaxis of ischemic disease.

16 Claims, 3 Drawing Sheets

SEQUENCE LISTING

```
<160> NUMBER OF SEQ ID NOS:    11

<210> SEQ ID NO 1
<211> LENGTH: 28
<212> TYPE: PRT
<213> ORGANISM: Homo sapiens

<400> SEQUENCE: 1

Ser Leu Arg Arg Ser Ser Cys Phe Gly Gly Arg Met Asp Arg Ile Gly
1               5                   10                  15

Ala Gln Ser Gly Leu Gly Cys Asn Ser Phe Arg Tyr
            20                  25

<210> SEQ ID NO 2
<211> LENGTH: 28
<212> TYPE: PRT
<213> ORGANISM: rat

<400> SEQUENCE: 2

Ser Leu Arg Arg Ser Ser Cys Phe Gly Gly Arg Ile Asp Arg Ile Gly
1               5                   10                  15

Ala Gln Ser Gly Leu Gly Cys Asn Ser Phe Arg Tyr
            20                  25

<210> SEQ ID NO 3
<211> LENGTH: 22
<212> TYPE: PRT
<213> ORGANISM: frog

<400> SEQUENCE: 3

Cys Phe Gly Gly Arg Met Asp Arg Ile Gly Ala Gln Ser Gly Leu Gly
1               5                   10                  15

Cys Asn Ser Phe Arg Tyr
            20

<210> SEQ ID NO 4
<211> LENGTH: 32
```

```
<212> TYPE: PRT
<213> ORGANISM: Homo sapiens

<400> SEQUENCE: 4

Ser Pro Lys Met Val Gln Gly Ser Gly Cys Phe Gly Arg Lys Met Asp
 1               5                  10                  15

Arg Ile Ser Ser Ser Gly Leu Gly Cys Lys Val Leu Arg Arg His
            20                  25                  30

<210> SEQ ID NO 5
<211> LENGTH: 24
<212> TYPE: PRT
<213> ORGANISM: frog

<400> SEQUENCE: 5

Ser Ser Asp Cys Phe Gly Ser Arg Ile Asp Arg Ile Gly Ala Gln Ser
 1               5                  10                  15

Gly Met Gly Cys Gly Arg Arg Phe
            20

<210> SEQ ID NO 6
<211> LENGTH: 32
<212> TYPE: PRT
<213> ORGANISM: porcine

<400> SEQUENCE: 6

Ser Pro Lys Thr Met Arg Asp Ser Gly Cys Phe Gly Arg Arg Leu Asp
 1               5                  10                  15

Arg Ile Gly Ser Leu Ser Gly Leu Gly Cys Asn Val Leu Arg Arg Tyr
            20                  25                  30

<210> SEQ ID NO 7
<211> LENGTH: 45
<212> TYPE: PRT
<213> ORGANISM: rat

<400> SEQUENCE: 7

Ser Gln Asp Ser Ala Phe Arg Ile Gln Glu Arg Leu Arg Asn Ser Lys
 1               5                  10                  15

Met Ala His Ser Ser Ser Cys Phe Gly Gln Lys Ile Asp Arg Ile Gly
            20                  25                  30

Ala Val Ser Arg Leu Gly Cys Asp Gly Leu Arg Leu Phe
        35                  40                  45

<210> SEQ ID NO 8
<211> LENGTH: 29
<212> TYPE: PRT
<213> ORGANISM: chicken

<400> SEQUENCE: 8

Met Met Arg Asp Ser Gly Cys Phe Gly Arg Arg Ile Asp Arg Ile Gly
 1               5                  10                  15

Ser Leu Ser Gly Met Gly Cys Asn Gly Ser Arg Lys Asn
            20                  25

<210> SEQ ID NO 9
<211> LENGTH: 22
<212> TYPE: PRT
<213> ORGANISM: Homo sapiens, porcine, rat

<400> SEQUENCE: 9

Gly Leu Ser Lys Gly Cys Phe Gly Leu Lys Leu Asp Arg Ile Gly Ser
```

-continued

```
                1               5                  10                 15
Met Ser Gly Leu Gly Cys
            20

<210> SEQ ID NO 10
<211> LENGTH: 22
<212> TYPE: PRT
<213> ORGANISM: chicken

<400> SEQUENCE: 10

Gly Leu Ser Arg Ser Cys Phe Gly Val Lys Leu Asp Arg Ile Gly Ser
1               5                  10                 15

Met Ser Gly Leu Gly Cys
            20

<210> SEQ ID NO 11
<211> LENGTH: 22
<212> TYPE: PRT
<213> ORGANISM: frog

<400> SEQUENCE: 11

Gly Tyr Ser Arg Gly Cys Phe Gly Val Lys Leu Asp Arg Ile Gly Ala
1               5                  10                 15

Phe Ser Gly Leu Gly Cys
            20
```

TREATMENT OR PROPHYLAXIS OF ISCHEMIC HEART DISEASE

FIELD OF THE INVENTION

This applications claims priority of Japanese Application No. 98134/2000, filed on Mar. 31, 2000. This invention relates to a pharmaceutical composition for reducing an infarct region resulting from the ischemic necrosis of cells, the pharmaceutical composition containing a substance, as an active ingredient, which can increase intracellular cGMP production by acting on a natriuretic peptide receptor.

This invention relates to a pharmaceutical composition for reducing an infarct region resulting from the ischemic necrosis of cells, the pharmaceutical composition containing a substance, as an active ingredient, which can increase intracellular cGMP production by acting on a natriuretic peptide receptor.

This invention also relates to a method for reducing an infarct region resulting from the ischemic necrosis of cells, comprising administering said substance or pharmaceutical composition to a patient with ischemic disease.

BACKGROUND OF THE INVENTION

In recent years, ischemic heart disease has posed a major problem in an aging population. Of cardiac diseases which are diseases of circulatory organs, myocardial infarction ascribed to cardiovascular disorder, in particular, is a serious, potentially fatal disease which either obstructs the coronary artery or substantially decreases the blood flow resulting in ischemic necrosis of myocytes and deteriorating cardiac function. The direct cause of myocardial infarction is a decrease or interruption of the blood flow to the myocardium due to coronary arteriosclerosis or thrombus formation in the coronary artery. The disease can result in either acute or chronic cardiac failure. Methods adopted for treatment of ischemic heart disease include the dilatation of the obstructed coronary artery by use of an intravascularly inserted balloon, maintenance of blood flow by intravascular insertion of a stent, and dissolution and removal of a thrombus formed in the blood vessel with the use of a thrombolytic agent. With any of such treatments, it is known that as blood flow is restored in the coronary artery, Ca overload or free radicals occur, increasing the region of cellular necrosis. Prevention of the occurrence of such ischemia-reperfusion injury is difficult, and no effective method of treatment has been established.

SUMMARY OF THE INVENTION

The present invention provides a pharmaceutical composition for reducing an infarct region resulting from the ischemic necrosis of cells, the pharmaceutical composition containing a substance, as an active ingredient, which can increase intracellular cGMP production by acting on a natriuretic peptide receptor.

The present invention also provides a method for reducing an infarct region resulting from the ischemic necrosis of cells, comprising administering said substance or pharmaceutical composition to a patient with ischemic disease.

More specifically, the invention provides a pharmaceutical composition and a method for suppressing ischemia-reperfusion injury in the treatment of ischemic disease.

Figure 1:
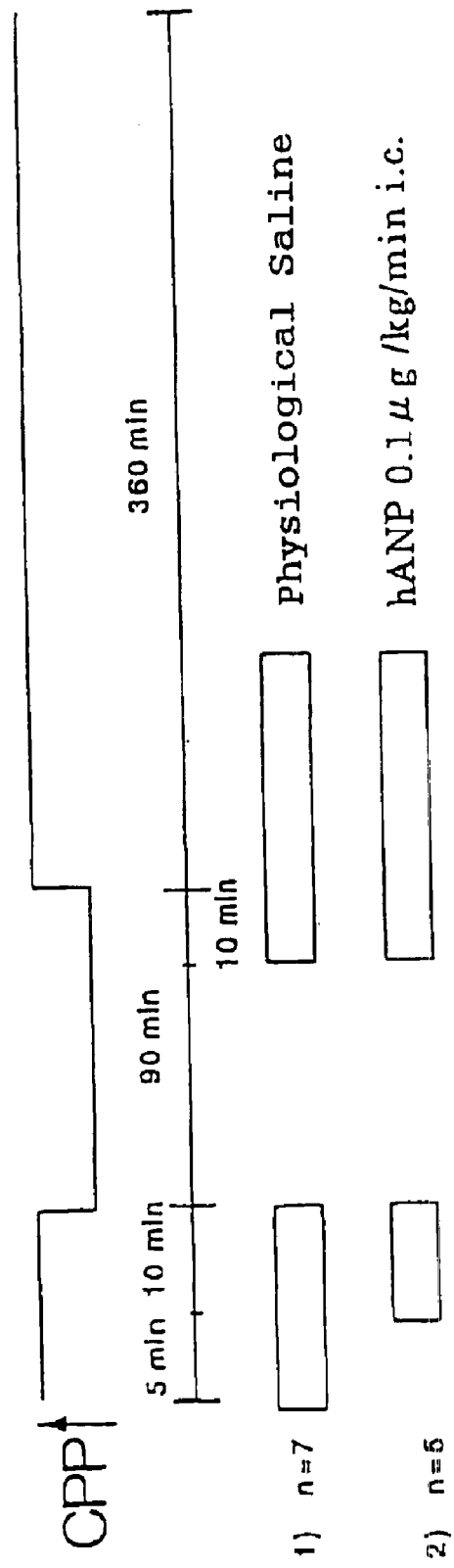
FIG. 1 is a view illustrating acute myocardial infarction models of Example, showing the state of ischemia-reperfusion, and the mode of administration in 1) a physiological saline treatment group (B group), and 2) an hANP treatment group (A group)

DETAILED DESCRIPTION OF THE INVENTION hANP, a natriuretic peptide, is used as an agent of symptomatic therapy for alleviating symptoms of cardiac failure, because it has a diuretic action, and exhibits a blood pressure lowing effect by promoting production of cGMP, which is considered to be a second messenger of relaxation in vascular smooth muscle cells, to induce relaxation of blood vessels (e.g., coronary artery).

The inventors of the present invention further studied the properties of natriuretic peptides, and found for the first time that these peptides can reduce an infarct region occurring in a model of acute myocardial infarction involving ischemia reperfusion. This finding led them to accomplish this invention.

That is, the present invention relates to a pharmaceutical composition for use in the treatment or prophylaxis of ischemic heart disease, such as myocardial infarction, the pharmaceutical composition containing a substance, as an active ingredient, which can increase intracellular cGMP production by acting on a natriuretic peptide receptor, and which has the effect of reducing an infarct region. In the present invention, "to reduce an infarct region" means to suppress enlargement of an infarct region.

The present invention also relates to a method for treatment or prophylaxis of ischemic disease, comprising administering a substance to a patient with ischemic disease, which substance can increase intracellular cGMP production by acting on a natriuretic peptide receptor, and which has the effect of reducing an infarct region. The method of the present invention is especially effective for suppressing ischemia-reperfusion injury.

Whether a certain substance can become the active ingredient of a pharmaceutical composition for use in the treatment or prophylaxis of ischemic disease, the pharmaceutical composition related to the present invention, can be investigated by using a known method, for example, the methods described in Minamitake, Y., et al., Biochem. Biophys. Res. Commun., 172, 971–978 (1990); Furuya, M., et al., Biochem. Biophys. Res. Commun., 170, 201–208 (1990); Furuya, M., et al., Biochem. Biophys. Res. Commun., 177, 927–931 (1991); Hidaka, H. et al., Folia Pharmacologica Japonica, 101, 309–325 (1993).

Preferred as the substance as an active ingredient according to the present invention are natriuretic peptides such as atrial natriuretic peptide (ANP), brain natriuretic peptide (BNP) and C-type natriuretic peptide (CNP). Of them, ANP and BNP are preferred, and ANP is the most preferred.

As ANP, there can be used human ANP (human atrial natriuretic peptide; hANP, Kangawa et al., Biochem. Biophys. Res. Commun., Vol. 118, p. 131, 1984) (Seq. ID No. 1) or rat ANP (Kangawa et al., Biochem. Biophys. Res. Commun., Vol. 121, p. 585, 1984) (Seq. ID No. 2), each ANP comprising 28 amino acids. The peptide as the active ingredient in the present invention may be a peptide having a ring structure of ANP (formation of a disulfide bond based on Cys), and a C-terminal portion succeeding the ring structure. An example of such a peptide is a peptide having amino acid residues at the 7-position to the 28-position of ANP (Seq. ID No. 3). Another example is frog ANP (Seq. ID No. 5). Of them, human ANP (hANP) is particularly preferred.

An example of BNP is human BNP comprising 32 amino acids and involving the formation of a disulfide bond, like the above-described ANP (Sudoh et al., Biochem. Biophys. Res. Commun., Vol. 159, p. 1427, 1989) (Seq. ID No. 4). Various BNP's of the origin other than human, such as pig BNP (Seq. ID No. 6) and rat BNP (Seq. ID No. 7), are also known, and can be used similarly. A further example is chicken BNP (Seq. ID No. 8).

Examples of CNP are pig CNP comprising 22 amino acids and involving the formation of a disulfide bond, like the above-described ANP and BNP (Sudoh et al., Biochem. Biophys. Res. Commun., Vol. 168, p. 863, 1990) (Seq. ID No. 9; human and rat also have the same amino acid sequence), chicken CNP (Arimura et al., Biochem. Biophys. Res. Commun., Vol. 174, p. 142, 1991) (Seq. ID No. 10), and frog CNP (Yoshihara et al., Biochem. Biophys. Res. Commun., Vol. 173, p. 591, 1990) (Seq. ID No. 11).

Furthermore, any person skilled in the art can apply modification, such as deletion, substitution, addition or insertion, and/or chemical modification to amino acid residues in the amino acid sequence of a known natriuretic peptide (e.g., the aforementioned human ANP; hANP), as desired, by a known method. One skilled in the art can confirm that the resulting compound is a compound which has the activity of acting on a receptor of ANP to increase cGMP production. Derivatives having this activity, therefore, are included in the substance as an active ingredient which is administered to a patient in accordance with the method of the present invention. Moreover, the substances involved in the present invention are not restricted to the above peptides, as long as they are substances capable of acting on a natriuretic peptide receptor to increase intracellular cGMP production. These substances may be non-peptide compounds.

The substance as an active ingredient according to the present invention may be of a free type, or its pharmaceutically acceptable salt. The salt with an inorganic acid includes, for example, salts with hydrochloric acid, sulfuric acid, and phosphoric acid. The salt with an organic acid may, for example, be acid addition salts with formic acid, acetic acid, butyric acid, succinic acid, and citric acid. The salt may be in the form of a metal salt with sodium, potassium, lithium or calcium, or a salt with an organic base.

The substance as an active ingredient is preferably mixed with known pharmaceutically acceptable carriers, vehicles, or diluents, and administered by an administration method used generally for drugs, for example, an oral administration method, or a parenteral administration method, such as intravenous administration, intracoronary administration, intramuscular administration, or subcutaneous administration. The pharmaceutical composition of the present invention can be produced, for example, by mixing, as desired, the active ingredient, pharmaceutically acceptable carriers, flavors, vehicles, and stabilizers. To produce solid preparations for oral administration, such as tablets, capsules, granules, and fine granules, the following additives can be used: (1) vehicles such as lactose, starch, and microcrystalline cellulose, (2) binders such as hydroxypropylcellulose, and polyvinylpyrrolidone, (3) disintegrants such as starch and crosscarmellose sodium, (4) plasticizers such as macrogol and triethyl citrate, (5) lubricants such as magnesium stearate and talc, (6) coating materials such as hydroxypropyl methylcellulose, and Eudragit, and (7) taste correctives such as sucrose and mannitol, odor correctives, and colorants.

To produce injections, ophthalmic solutions, or transnasal preparations, the following additives can be added: (1) tonicity agents such as sodium chloride, D-mannitol, and D-sorbitol, (2) pH regulators such as hydrochloric acid and citric acid, (3) buffering agents such as sodium citrate, sodium acetate, and boric acid, and (4) soothing agents such as procaine hydrochloride; as well as stabilizers, and surface active agents. In consideration of the stability, etc. of the active ingredient, it can be selected whether the active ingredient should be formed into a preparation to be used after dissolution or suspension when required, or into a liquid preparation.

To produce preparations for external use, such as ointments and cataplasms, the following materials can be added: (1) bases such as liquid petrolatum, petrolatum, and hydrophilic ointments, (2) emulsifying agents such as polysorbate 80, and tragacanth, (3) preservatives such as sodium benzoate, and propyl p-hydroxybenzoate, and (4) soothing agents such as procaine hydrochloride, stabilizers, and surface active agents.

When the substance as an active ingredient is a natriuretic peptide, this peptide orally administered is degraded in the digestive tract, and thus this mode of administration is generally not effective. However, the peptide can be orally administered in the form of a preparation minimally degraded in the digestive tract, for example, microcapsules comprising the peptide, as the active ingredient, enclosed in a liposome. A mode of administration by absorption through the mucosa other than the digestive tract, such as the rectum or a sublingual area, is also possible. In this case, a dosage form, such as a suppository or a sublingual tablet, can be used for administration.

The dose of the pharmaceutical composition of the present invention differs according to the age, the body weight, the severity of symptoms of, and the route of administration in, a patient with myocardial infarction or a patient potentially developing myocardial infarction. When the substance as an active ingredient is a natriuretic peptide, the pharmaceutical composition can be administered at a dose of 0.1 μg/kg/min to 0.2 μg/kg/min, and is preferably administered in a dose of 0.025 μg/kg/min to 0.1 μg/kg/min, by the continuous intravenous route.

EXAMPLE

The following example shows that hANP, a natriuretic peptide, reduces the region of myocardial infarction occurring in models of acute myocardial infarction involving ischemia reperfusion.

Method

Thoracotomy was performed in 12 adult beagles weighing 14 to 23 kg under anesthesia with pentobarbital sodium, and hANP (0.1 μg/kg/min) was continuously administered for 10 minutes into the left anterior descending branch (LAD) of the coronary artery. Then, the LAD was completely obstructed into an ischemic state until the LAD was reperfused 90 minutes later. hANP (0.1 μg/kg/min) was continuously administered into the LAD over the course of 1 hour since 10 minutes before initiation of reperfusion. After 6 hours of reperfusion, a region at risk of developing infarction was evaluated by Evans blue staining, and the region of infarction was evaluated by TTC staining (Group A: 5 dogs). After 80 minutes of ischemia, the amount of endocardial collateral blood flow was measured by the microsphere method. A group receiving physiological saline, instead of hANP, into the LAD was provided as a control group (Group B: 7 dogs).

A protocol for the experiments is shown in FIG. 1. In the drawing, CPP denotes coronary perfusion pressure. The protocol shows that blood flowed in the LAD before start of the test, then the blood flow was interrupted for 90 minutes, then blood flow was restored again, and the test was completed at 360 minutes. The amount of endocardial collateral blood flow during ischemia, the mean blood pressure, and the heart rate were also measured to investigate whether or not these parameters took part in the effect of the hANP according to the present invention.

Figure 2:
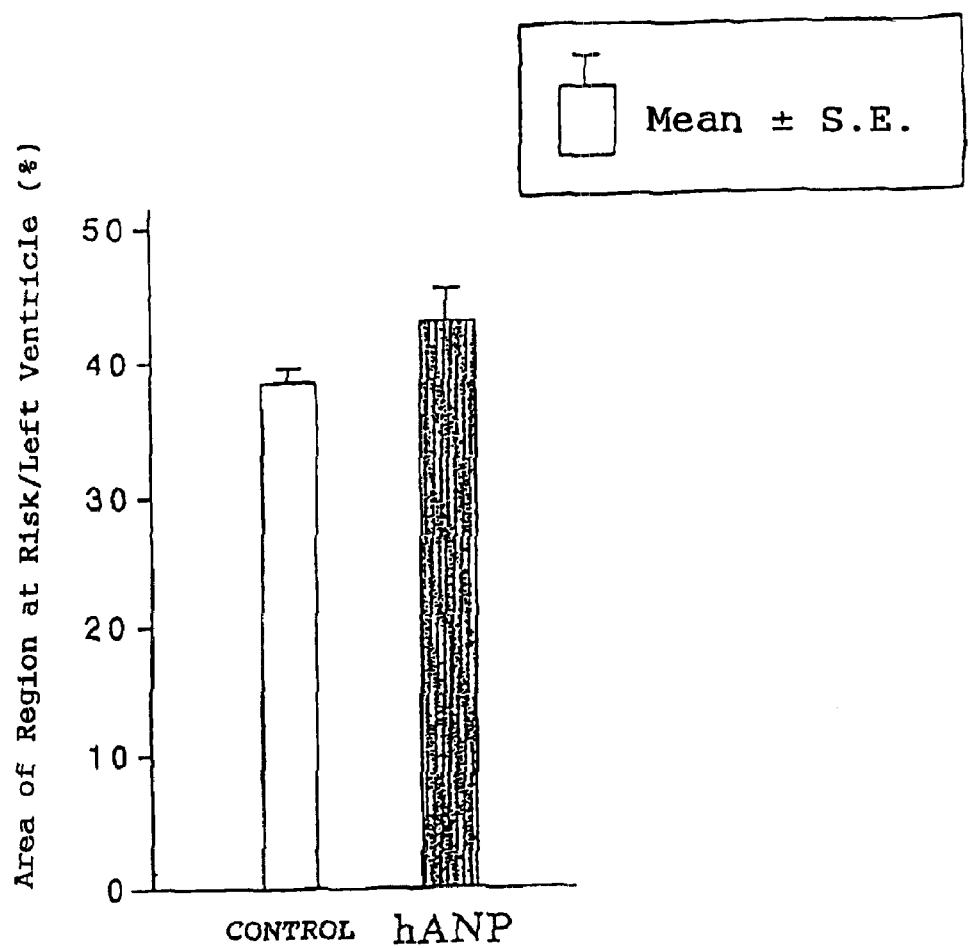
FIG. 2 is a view showing a region at risk for myocardial infarction in each group of the acute myocardial infarction models in FIG. 1.

Results (1) FIG. 2 shows the size of the region at risk of myocardial infarction in the left ventricle of each test group. There was no significant difference between the test groups in the size of the region at risk of myocardial infarction.

Figure 3:
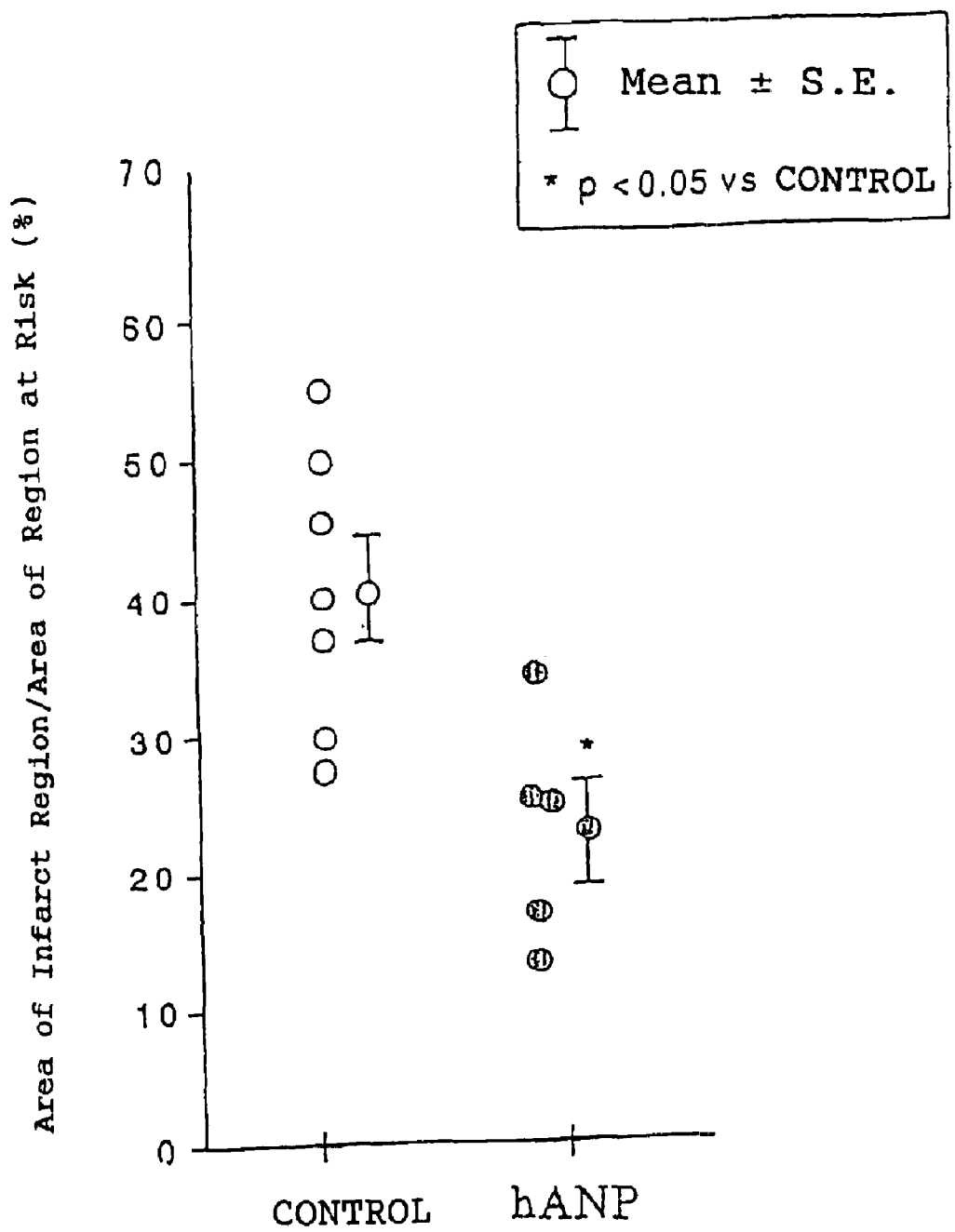
FIG. 3 is a view showing the ratio (%) of a region of myocardial infarction to the region at risk for myocardial infarction in each group.

(2) In the models of acute myocardial infarction involving ischemia reperfusion, the hANP administration reduced the region of myocardial infarction. As shown in FIG. 3, the region of myocardial infarction in the control group (Group B) was 41±3% of the region at risk of myocardial infarction, while the region of myocardial infarction significantly decreased to 21±5% in the hANP group (Group A).

(3) No difference was confirmed between the groups in terms of the amount of endocardial collateral blood flow during ischemia. Moreover, changes in the heart rate and the mean blood pressure in each group were measured 5 and 10 minutes after start of the test, 90 minutes after initiation of ischemia, and 360 minutes after start of reperfusion. The mean blood pressure and the heart rate were confirmed to remain unchanged following administration of hANP.

The above findings demonstrate that the administration of a natriuretic peptide suppresses ischemia-reperfusion injury in the treatment of ischemic disease. Thus, the effect of reducing the region of myocardial infarction is confirmed to be ascribed to the natriuretic peptide's action of reducing the region of myocardial infarction.

What is claimed is:

1. A method of treatment of ischemic heart disease, comprising administering to a patient in need of such a treatment a substance, as an active ingredient, which can increase intracellular cyclic guanosine 3',5'-monophosphate (cGMP) production by acting on a natriuretic peptide receptor, and which has an effect of reducing an infarct region, during and/or following ischemia reperfusion therapy.

2. The method of claim 1, wherein ischemia-reperfusion injury is reduced in the treatment of ischemic heart disease.

3. The method of claim 1, wherein the ischemic heart disease is myocardial infarction.

4. The method of claim 1, wherein the substance as the active ingredient is a natriuretic peptide or its salt.

5. The method of claim 4, wherein the natriuretic peptide is atrial natriuretic peptide (ANP), brain natriuretic peptide (BNP) or C-type natriuretic peptide (CNP).

6. A method of claim 5, wherein the natriuretic peptide is administered at a dose between 0.01 µg/kg/ml by continuous infusion.

7. A method of claim 6, wherein the natriuretic peptide is administered at a dose between 0.025 µg/kg/ml and 0.1 µg/kg/ml.

8. A method of any one of claims 5, 6, and 7, wherein administration is by an intravenous injection.

9. A method by any one of claims 5, 6 and 7, wherein administration is by a coronary injection.

10. A method for reducing an infarct region or suppressing enlargement of an infarct region in the heart of a patient who is suffering from infarct resulting from ischemic necrosis as an ischemia reperfusion injury, wherein said method comprises:
    administering a substance acting on a natriuretic peptide receptor to increase the production of cellular cyclic guanosine 3', 5'-monophosphate (cGMP), at an amount effective for reducing the infarct region or suppressing enlargement of an infarct region to said patient, during and/or following ischemia reperfusion.

11. The method of claim 10, wherein the substance as the active ingredient is a natriuretic peptide or its salt.

12. A method of claim 11, wherein the substance is a natriuretic peptide comprising atrial natriuretic peptide (ANP), brain natriuretic peptide (BNP) or C-type natriuretic peptide (CNP).

13. A method of claim 12, wherein the natriuretic peptide is administered at a dose between 0.01 µg/kg/ml and 0.2 µg/kg/ml by continuous infusion.

14. A method of claim 13, wherein the natriuretic peptide is administered at a dose between 0.025 µg/kg/ml and 0.1 µg/kg/ml.

15. A method of any one of claims 12, 13 and 14, wherein administration is by an intravenous injection.

16. A method by any one of claims 12, 13 and 14, wherein administration is by a coronary injection.

* * * * *

UNITED STATES PATENT AND TRADEMARK OFFICE
CERTIFICATE OF CORRECTION

PATENT NO. : 7,026,293 B2
APPLICATION NO. : 09/752724
DATED : April 11, 2006
INVENTOR(S) : Masafumi Kitakaze Page 1 of 1

It is certified that error appears in the above-identified patent and that said Letters Patent is hereby corrected as shown below:

On the title page: Item (73), change "DAIICHI SUNTORY PHARMA CO., LTD." to --DAIICHI ASUBIO PHARMA CO., LTD.--;

Signed and Sealed this

Fourteenth Day of October, 2008

JON W. DUDAS
*Director of the United States Patent and Trademark Office*